United States Patent
Dupps, Jr. et al.

(10) Patent No.: US 7,935,058 B2
(45) Date of Patent: May 3, 2011

(54) METHOD FOR MEASURING BIOMECHANICAL PROPERTIES IN AN EYE

(75) Inventors: William J. Dupps, Jr., Bay Village, OH (US); Andrew M. Rollins, Highland Heights, OH (US); Matthew Ford, Parma Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 158 days.

(21) Appl. No.: 11/807,079

(22) Filed: May 25, 2007

(65) Prior Publication Data

US 2008/0086048 A1 Apr. 10, 2008

Related U.S. Application Data

(60) Provisional application No. 60/808,788, filed on May 26, 2006, provisional application No. 60/875,727, filed on Dec. 19, 2006.

(51) Int. Cl.
*A61B 3/10* (2006.01)
*A61B 3/107* (2006.01)

(52) U.S. Cl. .......................... 600/405; 600/398; 600/399

(58) Field of Classification Search .................. 600/398, 600/399, 400 M, 401, 402, 403, 404, 405, 600/406, 400
See application file for complete search history.

(56) References Cited

U.S. PATENT DOCUMENTS

| | | | |
|---|---|---|---|
| 5,115,808 A | 5/1992 | Popovic et al. | |
| 5,810,731 A | 9/1998 | Sarvazyan et al. | |
| 5,911,694 A * | 6/1999 | Ikeda et al. | 600/587 |
| 5,936,731 A | 8/1999 | Cabib et al. | |
| 6,030,343 A | 2/2000 | Chechersky et al. | |
| 6,083,160 A * | 7/2000 | Lipman | 600/398 |
| 6,120,444 A * | 9/2000 | Miyakawa et al. | 600/401 |
| 6,168,572 B1 | 1/2001 | Vexler et al. | |
| 6,673,014 B2 * | 1/2004 | Badehi et al. | 600/398 |
| 7,003,143 B1 * | 2/2006 | Hewitt et al. | 382/128 |
| 7,365,856 B2 | 4/2008 | Everett et al. | |
| 2002/0171804 A1 | 11/2002 | Rathjen | |
| 2002/0173712 A1 * | 11/2002 | Feldon et al. | 600/405 |
| 2003/0103212 A1 * | 6/2003 | Westphal et al. | 356/479 |
| 2003/0187343 A1 * | 10/2003 | Cuzzani et al. | 600/399 |
| 2004/0068192 A1 * | 4/2004 | Westphal et al. | 600/476 |
| 2005/0168445 A1 * | 8/2005 | Piot et al. | 345/163 |
| 2006/0013473 A1 * | 1/2006 | Woodfill et al. | 382/154 |
| 2006/0058592 A1 * | 3/2006 | Bouma et al. | 600/301 |
| 2006/0084856 A1 * | 4/2006 | Biggins et al. | 600/399 |
| 2006/0241367 A1 * | 10/2006 | Koest | 600/405 |

FOREIGN PATENT DOCUMENTS

EP 1 402 810 A1 3/2004
WO WO 00/25662 A1 5/2000

* cited by examiner

*Primary Examiner* — Max Hindenburg
*Assistant Examiner* — Michael C Stout
(74) *Attorney, Agent, or Firm* — Tarolli, Sundheim, Covell & Tummino LLP

(57) ABSTRACT

Systems and methods are provided for characterizing biomechanical properties of tissue within an eye. A perturbation component introduces a stress to the eye tissue. An imaging component is operative to obtain an image of the eye tissue. A first image of the tissue can be obtained prior to the introduction of the stress and a second image of the tissue can be obtained after the introduction of the stress. An image analysis component compares the first image and the second image as to determine at least one biomechanical property of the tissue.

15 Claims, 4 Drawing Sheets

METHOD FOR MEASURING BIOMECHANICAL PROPERTIES IN AN EYE

RELATED APPLICATIONS

This application claims priority from U.S. Provisional Application Nos. 60/808,788, filed May 26, 2006 and 60/875,727, filed Dec. 19, 2006, the subject matter of which is incorporated herein by reference.

FIELD OF THE INVENTION

The present invention relates to a system and method for non-invasive sensing of living tissue and, in particular, is directed to systems and methods for non-invasively measuring biomechanical properties of the eye.

BACKGROUND OF THE INVENTION

The cornea relies greatly upon its material properties in its roles as a mechanical barrier to injury and as a scaffold for the eye's primary refracting surface. These biomechanical properties influence the safety and optical predictability of surgery and play an important role in the pathogenesis and of diseases such as keratoconus and post-refractive surgery ectasia. Consequently, alteration of these properties by disease or surgery can have profound visual implications. Ectatic diseases such as keratoconus, pellucid marginal degeneration and keratoglobus are characterized by progressive thinning and distortion of the cornea, and as a class represent a leading indication for corneal transplantation. Identification of early ectasia is a major emphasis of preoperative refractive surgery evaluations, where it is imperative to avoid the potential destabilizing effects of laser vision correction in corneas that are predisposed to biomechanical instability or failure.

Current screening tools are hampered by a reliance on late features of disease and a lack of tools for detecting subclinical abnormalities of elastic or viscoelastic behavior. In addition to playing a key role in the pathophysiology of keratectasia, corneal biomechanical properties influence the predictability of optical outcomes after laser in-situ keratomileusis (LASIK), photorefractive keratectomy (PRK) and other corneal surgeries. Corneal rigidity is also a poorly-characterized confounder of clinical intraocular pressure (IOP) measurement, and therefore its measurement has great relevance in the diagnosis and management of glaucoma.

SUMMARY OF THE INVENTION

In accordance with an aspect of the present invention, a system is provided for characterizing biomechanical properties of tissue within an eye. A perturbation component introduces a stress to the eye tissue. An imaging component is operative to obtain an image of the eye tissue. A first image of the tissue can be obtained prior to the introduction of the stress and a second image of the tissue can be obtained after the introduction of the stress. An image analysis component compares the first image and the second image as to determine at least one biomechanical property of the tissue.

In accordance with another aspect of the present invention, an apparatus is provided for applying a controlled stress to tissue within an eye. The apparatus includes a chamber having a surface that is optically transparent along at least a portion of its surface area and an opening, positioned opposite to the surface, that can be positioned over at least a portion of the eye. A pump is operatively connected to the chamber such that the pressure within the chamber can be altered by the pump. A pressure transducer measures the pressure within the chamber. A system control controls the pump in response to the measured pressure as to deliver a desired pressure within the chamber.

In accordance with yet another aspect of the present invention, a method is provided for characterizing biomechanical properties of tissue within an eye. A first image of the eye tissue is obtained. A stress is introduced to the eye tissue, and a second image of the eye tissue is obtained while the eye is under stress. The first and second images are compared to determine at least one biomechanical property of the eye tissue.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
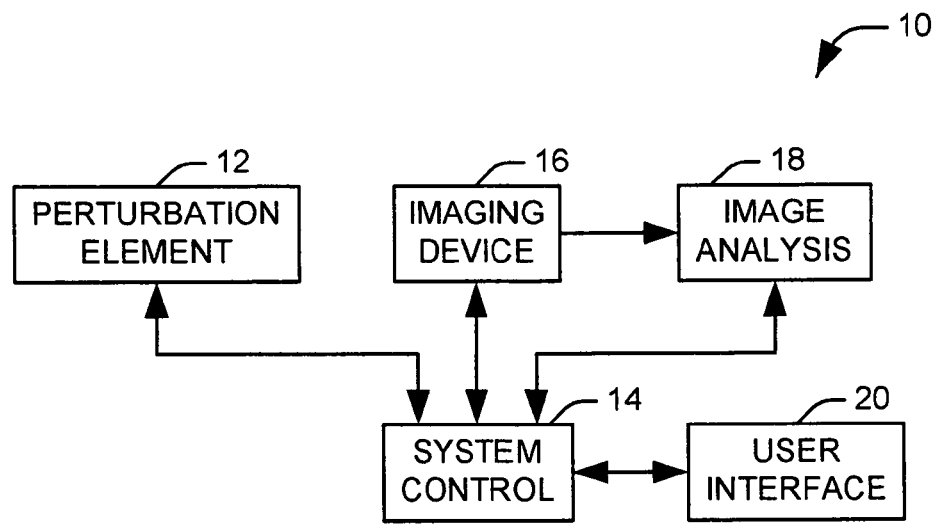
FIG. 1 illustrates a system for non-invasive determination of biomechanical properties of the eye in accordance with an aspect of the present invention.

FIG. 1 illustrates a system 10 for non-invasive determination of biomechanical properties of eye tissue in accordance with an aspect of the present invention. The system 10 comprises a perturbation element 12 that is operative to cause movement within a desired potion of the eye tissue when directed by a system control 14. The perturbation element 12 can comprise any appropriate mechanism for applying stress or displacement to the eye, for example, devices for establishing a region of altered air pressure at the surface of the eye, speakers for producing acoustic perturbations of the eye tissue, or deforming devices that physically contact the eye to provide a stress or displacement.

An imaging device 16 is operative to obtain a non-invasive image of the eye tissue. It will be appreciated that the imaging device can be operative to image tissue below the surface of the eye, such that information related to the various corneal layers and other ocular layers can be obtained. For example, an optical coherence tomography (OCT) scanner can be utilized over a predetermined scan pattern covering the desired portion of the eye to produce the images. The images can then be provided to an image analysis element 18, where the data produced by the imaging device can be interpreted and provided in a form comprehensible to a user via a user interface 20. In one implementation, the image analysis element 18 is implemented at least in part, as a software program, stored on a computer readable medium that is executed by a general purpose processor.

During operation, the system control 14 can instruct the imaging system 16 to take a first, baseline image of the eye tissue according to a scan pattern comprising a plurality of desired scan locations. It will be appreciated that the system control 14 can be implemented, at least in part, as a software program, stored on a computer readable medium that is executed by a general purpose processor. The perturbation element 12 can then be instructed to apply a predetermined amount of stress or displacement to the eye tissue, and a second image of the eye tissue at each of the desired locations can be obtained. For example, the predetermined amount of stress or displacement can comprise a known power and/or frequency of sound waves, pressure differential, or mechanical displacement. This can be repeated for multiple levels of stress or displacement with accompanying images of the eye tissue obtained for each stress level. The scan pattern defining the plurality of locations as well as the stress levels applied to the eye can be provided in a configuration file or selected by the user via the user interface 20. It will be appreciated that the system control 14 can also utilize specific sequences of stress or displacement levels to facilitate measurement of certain biomechanical properties of the eye. For example, specific patterns of stress levels can be applied to facilitate construction of stress-strain curves, analysis of non-linear elastic modulus, measurement of stress relaxation time constants for viscoelastic measurement, assessment of hysteresis, and assessment of poroelastic behavior within the tissue.

Once the images are obtained and constructed according to the selected scan pattern, they can be compared to one another at the image analysis element 18 to determine a magnitude and direction of displacement in the eye tissue for a given level of stress. It will be appreciated that the image data provides a three-dimensional representation of the eye tissue, such that the displacement of the eye tissue can be evaluated in one, two, or three dimensions. Each image can be compared to the baseline image to determine the displacement caused by its associated stress level. When performed for each of a plurality of scanning locations, the analysis can be used to provide a three-dimensional representation of the biomechanical properties of the eye tissue. Parameters calculated from the determined displacements can be used, for example, in predicting a patient's response to surgery or for identifying risk factors for glaucoma or corneal ectatic disorders such as keratoconus and pellucid marginal degeneration.

Figure 2:
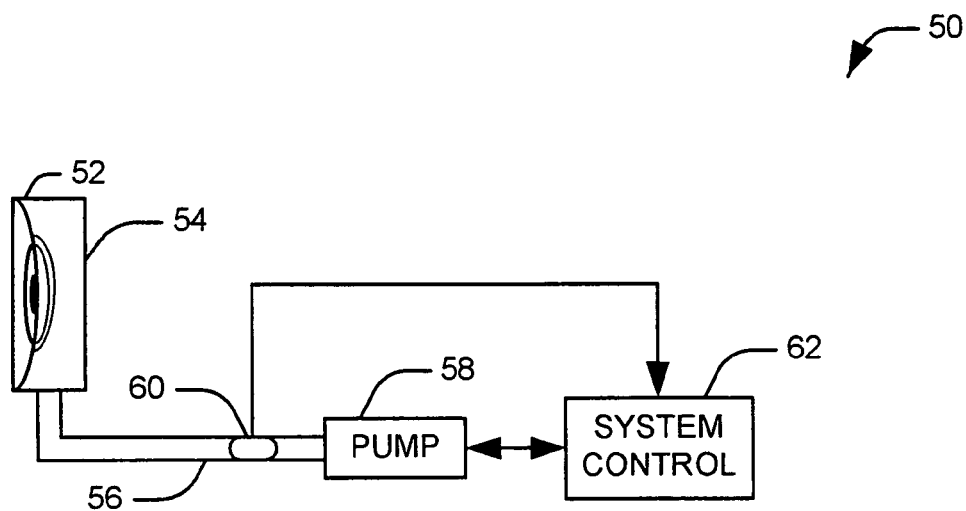
FIG. 2 illustrates an apparatus for applying stress to an eye in accordance with an aspect of the present invention.

FIG. 2 illustrates an apparatus 50 for applying stress to an eye in accordance with an aspect of the present invention. The apparatus includes an optically transparent chamber 52 that can be positioned over at least a portion of the eye. It will be appreciated that the optically transparent chamber 52 need only be transparent along at least a portion of a surface 54 opposing the eye, such that imaging of the eye can take place through the chamber. Accordingly, at least some portion of the optically transparent chamber 52 can be opaque or translucent. In one implementation, the surface 54 opposing the eye can be designed to couple with a portion of a scanner (e.g., an OCT scanner or an ultrasound scanner) as to reduce distortion due to motion during a scan of the eye.

In accordance with an aspect of the present invention, the chamber 52 can be an open-ended airtight container that is designed to be safely attached to skin or eye tissue via suction, adhesives or a mechanical force (e.g., an elastic strap). For example, a pressure goggle can be utilized placed over the entire eye, such that the goggle rests at a position corresponding approximately to the orbital bone structure surrounding the eye. A port can be included within the goggle to allow a user to connect an air pump, such that the pressure within the goggle can be controlled to apply positive or negative pressure to the eye, or an oscillation between positive and negative pressure to the eye.

Figure 3:
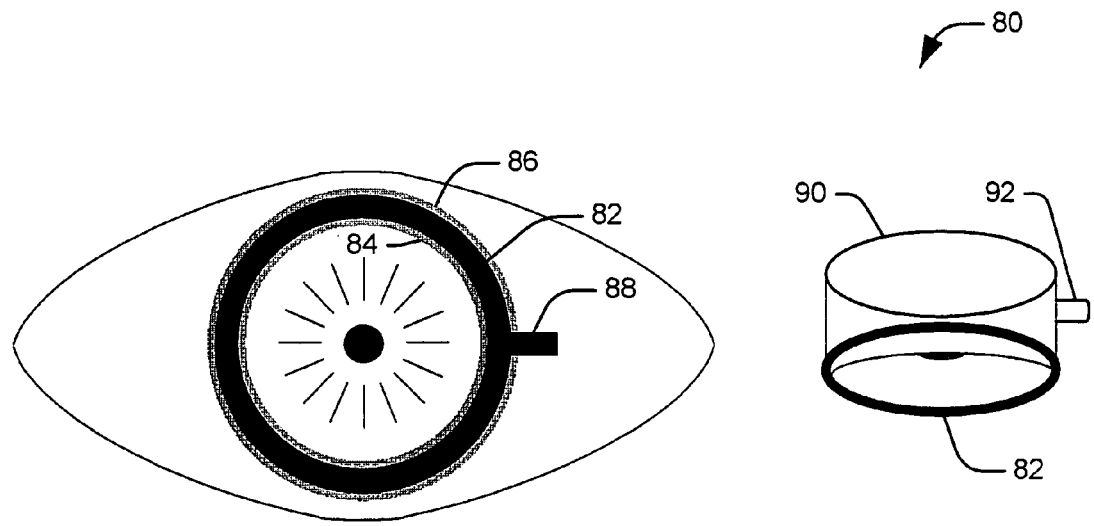
FIG. 3 illustrates a scleral ring assembly that can be utilized to apply a localized stress to tissue within a desired portion of an eye.

Alternatively, a chamber can be designed to produce a localized stress on a desired portion of the eye tissue. FIG. 3 illustrates a scleral ring assembly 80 that can be utilized to apply a localized stress to tissue within a desired portion of an eye. The scleral ring 80 comprises an annular base portion 82 that can be positioned on the surface of the eye to encircle a desired region of tissue (e.g., around the iris). To protect the eye tissue, soft skirts 84 and 86 of a soft material (e.g., silicone) can extend from the inner and outer diameters of the annular base portion 82. The annular base portion 82 further comprises a port 88 that is operative to receive a syringe. During use, an optically transparent chamber 90 can be mounted on the annular base portion 82. A syringe can then be inserted into the port 88, and air can be withdrawn from the annular base portion 82, fixating the annular base portion to the eye via suction. The pressure within the optically transparent chamber 90 can be controlled via pump or similar apparatus via a port 92 in the side of the chamber to apply a stress to the eye.

Returning to FIG. 2, the optically transparent chamber 52 can be connected via an airtight connector 56 to a pump 58 that controls the pressure within the chamber. The pump 58 can be implemented as any appropriate apparatus that will allow precise control of pressure within the chamber 52, for example, a micromotored pump assembly. A pressure transducer 60 can be positioned within the connector 56 to obtain feedback as to the actual pressure within the chamber 52. This feedback can be provided to a system control 62 which controls the pump 58 to deliver a desired pressure in response to the measured feedback.

Figure 4:
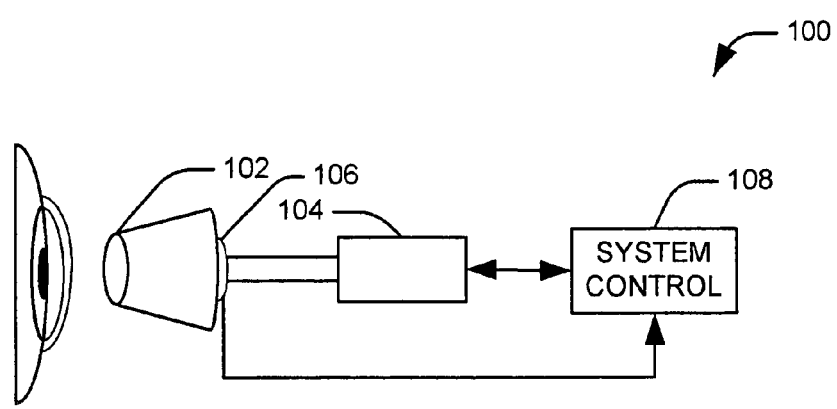
FIG. 4 illustrates an exemplary implementation of a system for non-invasive determination of biomechanical properties of the eye in accordance with an aspect of the present invention.

FIG. 4 illustrates an exemplary implementation of a system 100 for non-invasive determination of biomechanical properties of the eye in accordance with an aspect of the present invention. The system 100 includes an optically transparent lens 102 that can be brought into contact with the surface of the eye to apply a mechanical force to the eye. The lens can take on any appropriate shape for applying a desired stress or displacement to the eye, for example, a flat lens or a lens curved to approximate the contour of the cornea. In accordance with an aspect of the present invention, the imaging system can be configured to operate through the lens.

A micromotor apparatus 104 can be utilized to move the applanation lens 102 as to apply a desired degree of stress or displacement to the eye tissue. The degree of stress applied to the eye can be measured by a stress gauge 106, with the stress gauge measurements fed back to a system control 108. The system control 108 regulates the operation of the micromotor 104 as part of a closed loop system to maintain a desired level of stress on the eye tissue. The system control 108 can alter the stress level dynamically according to user input or a configuration file as to obtain images representing a plurality of different stress levels applied to the eye tissue.

Figure 5:
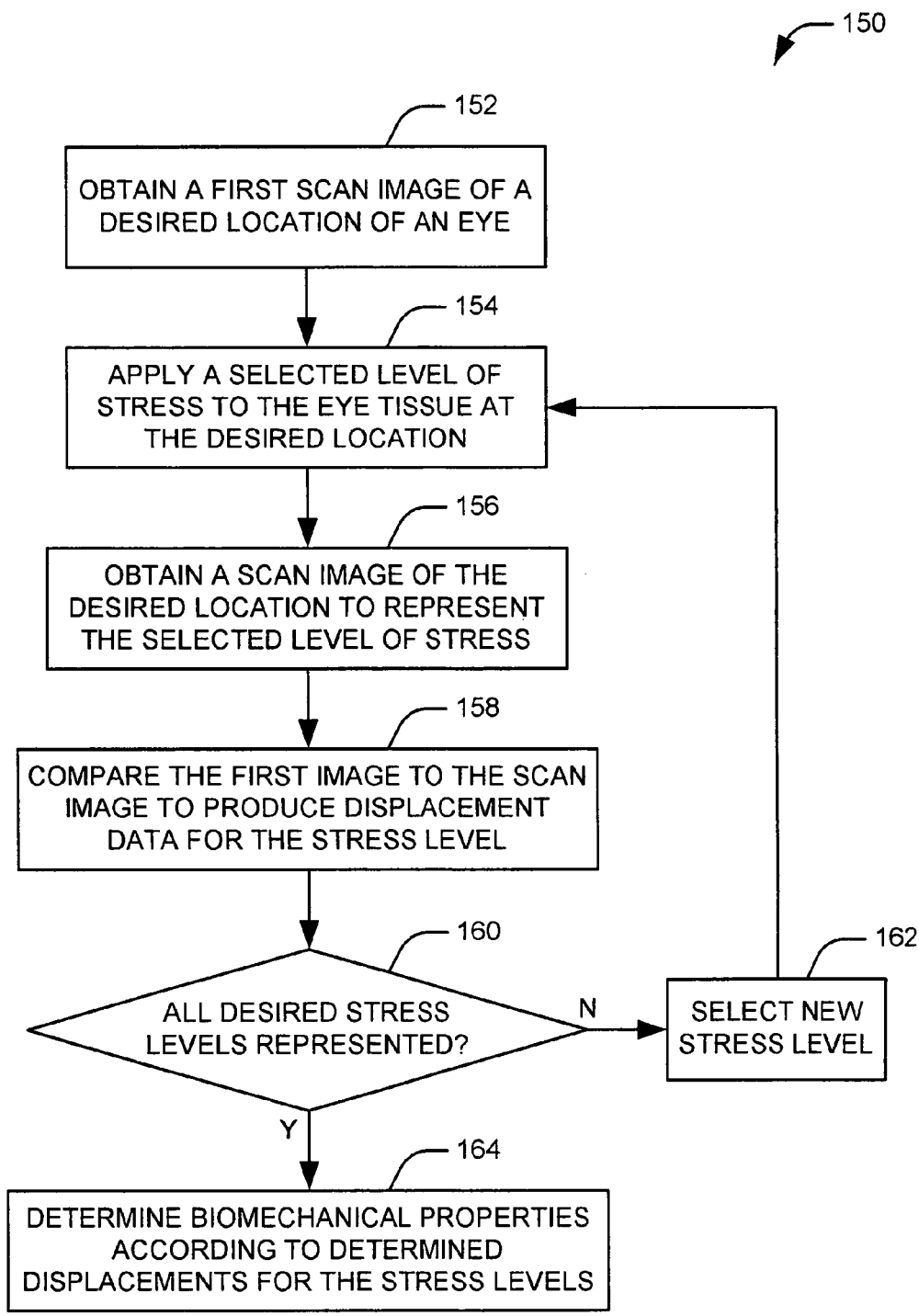
FIG. 5 illustrates a methodology for non-invasively determining biomechanical properties of eye tissue in accordance with an aspect of the present invention.
Figure 6:
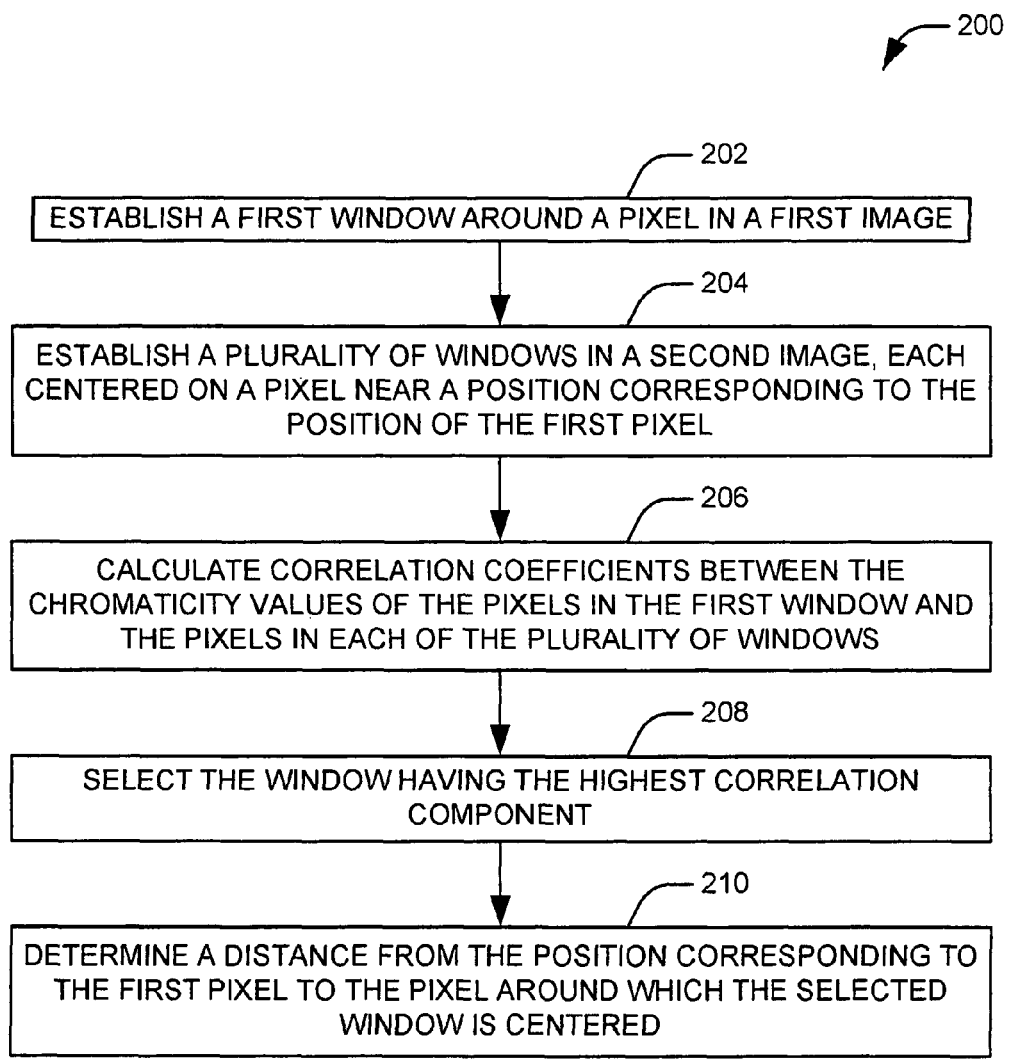
FIG. 6 illustrates an exemplary methodology for determining a relative displacement of eye tissue represented by two images in accordance with an aspect of the present invention.

In view of the foregoing structural and functional features described above, methodologies in accordance with various aspects of the present invention will be better appreciated with reference to FIGS. 5 and 6. While, for purposes of simplicity of explanation, the methodology of FIGS. 5 and 6 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 5 illustrates an exemplary methodology 150 for non-invasively determining biomechanical properties of eye tissue in accordance with an aspect of the present invention. The methodology 150 begins at step 152, where a first image is obtained of a desired location of an eye. This can be accomplished by any appropriate system for non-invasive, three-dimensional imaging of the eye. In an exemplary implementation, the image is obtained via an optical coherence tomography (OCT) scanner. At step 154, a selected level of stress is applied to the eye tissue at the desired location. This can be accomplished by mechanical force (e.g., via an applanation system), via acoustic perturbance at one or more frequencies, or via an applied air pressure. The level of stress applied can be quantified by a transducer that measures the applied air pressure, by known decibel levels of the applied sound, or via a strain gauge on a mechanical system. The level of stress to be applied can be selected by a user via a user interface or preselected as part of a configuration file. An image of the desired location can be taken while the stress is being applied at step 156 to obtain an image representing the selected stress level. It will be appreciated that the first image and the scan image can be frames in a continuous video in the scanning modality.

At step 158, the first image is compared to the scan image representing the selected stress level to produce displacement data for the selected stress level. In an exemplary embodiment, a correlation process can be used to match selected locations of the first image with locations on the scan image, and a displacement value can be calculated for each of the selected locations from the matching locations on the scan image. At step 160, it is determined if all desired stress levels have representative displacement measurements. If not, the methodology proceeds to step 162 to select a new stress level and returns to step 154 to obtain an image representing the new stress level. If all stress levels are represented, one or more parameters representing biomechanical properties of the eye can be calculated from the determined displacement values at step 164. The calculated parameters can represent all or a selected portion of the scanned portion of the eye and can include stress-strain curves, non-linear elastic modulus values, stress relaxation time constants for viscoelastic measurement, hysteresis, and poroelastic parameters.

This validity of the methodology has been verified empirically by trials on donated human globes. A laboratory-based high-speed Fourier-domain optical coherence tomography scanner (OCT) was used to image each eye while intraocular pressure (IOP) was decreased from 20 to 13±1 mmHg in replicate experiments (5 per eye). The pressure was directly controlled and monitored by intravitreal infusion. The displacement at three regions of interest was measured from the images, and the measured displacement was compared via paired t-tests across the replicate experiments.

The measured axial displacement was found to exhibit statistically significant differences even in eyes from the same donor. In some cases, smaller displacements were found to occur in anterior stromal regions than in posterior stromal regions, while differences between laterally separated regions in the central 3.3 mm of the cornea were small. Displacement magnitudes within each region of interest varied by less than 3 um on average during a single imaging sequence These results are consistent with ex vivo ultrastructural and biomechanical evidence for greater material strength in the anterior than the posterior stroma and much greater resistance to lateral strain than axial strain in the normal, un-incised cornea. The applied methodology exhibited has sufficient resolution and repeatability to detect differences in the local response to a physiologic stress within and between eyes of a same-donor pair, indicating that methodology should have sufficient sensitivity for detecting ectasia, evaluating the biomechanical effects of surgical and collagen stiffening interventions, accurately measuring intraocular pressure, and discerning preoperative material heterogeneity that could impact the optical response to surgery.

FIG. 6 illustrates an exemplary methodology 200 for determining a relative displacement of eye tissue represented by two images in accordance with an aspect of the present invention. Each image can be represented as a plurality of pixels, with each pixel having a corresponding chromaticity value. In an exemplary embodiment, the chromaticity value is a gray-scale intensity associated with the pixel, but other parameters can be used, depending on the imaging modality. For example, in an OCT implementation, a phase value can be extracted from the raw OCT images for high fidelity comparisons. The methodology 200 begins at step 202, where a first window of pixels is defined centered on a pixel of interest within the first image. The size of the window can vary, with larger windows allowing for superior accuracy at the cost of additional processing. In an exemplary implementation, a four pixel by four pixel window can be used.

At step 204, additional windows are defined at and around a point on the second image corresponding to the pixel of interest. For example, a number of windows can be defined centered on pixels around the point corresponding to the pixel of interest, such that each window represents a known displacement from that point. The additional windows are the same size and shape as the first window, such that each pixel in the first window has a corresponding pixel in each additional window.

At step 206, respective correlation coefficients are calculated between the chromaticity values in the first window and the chromaticity values in each of the plurality of windows defined in the second image. In the illustrated example, the correlation coefficient for each window in the second image can be calculated as:

$$C(x, y) = \frac{\sum_{x,y} [M(x, y) - \overline{M}][N(x, y) - \overline{N}]}{\sqrt{\sum_{x,y} [M(x, y) - \overline{M}]^2 \sum_{x,y} [N(x, y) - \overline{N}]^2}}$$

where C is the correlation coefficient, $\overline{M}$ is the average chromaticity value of pixels in the first window, $\overline{N}$ is the average chromaticity value of the window in the second image, x is a horizontal coordinate within each window, defined from the center point of the window, y is a vertical coordinate within each window, defined from the center point of the window, M(x,y) is the chromaticity value of the pixel at the coordinates x,y within the first window and N(x,y) is the chromaticity value of a pixel at coordinates x,y.

Once the correlation coefficients for each window have been calculated, a window having the highest correlation coefficient can be selected at step 208. It will be appreciated that the window in the second image having the highest correlation to the first window is most likely to represent the tissue represented in the first window. Accordingly, at step 210, the distance between the center pixel in the selected window and the position in the second image corresponding to the center pixel of the first window can be determined as a displacement value for the tissue at that location. It will be appreciated that this analysis can be repeated for multiple locations within the eye to determine the displacement at each location in response to a stress represented by the second image.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A system for characterizing biomechanical properties of tissue within an eye, comprising:
    a perturbation component, comprising a deforming lens that contacts the eye as to apply a stress to the eye tissue;
    an imaging component operative to obtain images of the eye tissue such that a first image of the tissue can be obtained prior to the introduction of the stress and a second image of the tissue can be obtained after the introduction of the stress; and
    an image analysis component that compares the first image and the second image as to determine at least one of a stress-strain curve representing the eye tissue, a non-linear elastic modulus value, a stress relaxation time constant, a value representing hysteresis, and a poroelastic parameter.

2. The system of claim 1, the perturbation component comprising a scleral ring that comprises:
    an annular base that can be positioned on the scleral tissue to encircle a desired portion of the eye;
    an optically transparent chamber that can be mounted on the annular base;
    a port on the annular base for receiving a syringe, such that the syringe can be actuated to generate a suction within the scleral ring as to fix the scleral ring to the eye.

3. The system of claim 1, the perturbation component comprising:
    an optically transparent goggle can be positioned around the eye, such that the goggle does not contact the tissue of the eye; and
    an air pump that is operatively connected to the optically transparent goggle such that the pressure within the goggle can be altered by the action of the pump.

4. The system of claim 1, the perturbation component further comprising:
    a strain gauge that measures the stress applied to the eye tissue by the deforming lens, the deforming lens being utilized by the imaging component to obtain at least one of the first and second images of the eye tissue.

5. The system of claim 1, the perturbation component comprising:
    an optically transparent chamber; and
    an air pump that is operatively connected to the optically transparent chamber such that the pressure within the optically transparent chamber can be altered by the pump.

6. The system of claim 5, further comprising:
    a pressure transducer that measures the pressure within the optically transparent chamber; and
    a system control that controls the pump in to response to the measured pressure to maintain a desired pressure within the chamber.

7. The system of claim 1, the imaging component comprising an optical coherence tomography (OCT) imaging system.

8. The system of claim 1, further comprising a system control that is configured to direct the perturbation component to introduce different amounts of stress on the eye tissue at different times such that images of the eye tissue can be obtained with the eye tissue subject to varying levels of stress.

9. The system of claim 1, wherein the image analysis component is operative to define at least one pixel window in the first image, to define a plurality of pixel windows in the second image, and to perform a correlation analysis, utilizing at least one chromaticity value associated with the pixels comprising each pixel window, to match each of the at least one pixel window in the first image with a pixel window in the second image.

10. The system of claim 1, the perturbation component comprising at least one speaker that applies acoustic perturbation to the eye tissue.

11. A method for characterizing biomechanical properties of tissue within an eye, comprising:
    obtaining a first image of the eye tissue at an imaging system;
    introducing a stress to the eye tissue;
    obtaining a second image of the eye tissue at the imaging system while the eye is under stress; and
    comparing the first and second images to determine at least one viscoelastic parameter wherein comparing the first and second images to determine at least one viscoelastic parameter of the eye comprises:
        defining at least one pixel window in the first image;
        defining a plurality of pixel windows in the second image;
        performing a correlation analysis, utilizing at least one chromaticity value associated with the pixels comprising each pixel window, to match each of the at least one pixel window in the first image with a pixel window in the second image;
        determining a displacement value associated with the stress level for each of the at least one pixel window in the first image from the respective matched windows in the second image;
        calculating at least one of a stress-strain curve representing the eye tissue, a non-linear elastic modulus value, a stress relaxation time constant, a value representing hysteresis, and a poroelastic parameter from the determined displacement values; and
    displaying the determined at least one viscoelastic parameter to a user at a user interface.

12. The method of claim 11, wherein introducing a stress to the eye tissue includes applying pressure to at least a portion of the eye with a mechanical applanation device.

13. The method of claim 11, wherein introducing a stress to the eye tissue includes exposing at least a portion of the eye to an volume of reduced air pressure as to produce a suction force on the eye tissue.

14. The method of claim 11, wherein obtaining a first image of the eye tissue comprises obtaining an image of the eye via optical coherence tomography.

15. The method of claim 11, wherein introducing a stress to the eye tissue comprises subjecting the eye tissue to an acoustic perturbation.

* * * * *